US010081876B2

(12) United States Patent
Horsthemke

(10) Patent No.: US 10,081,876 B2
(45) Date of Patent: Sep. 25, 2018

(54) AQUEOUS ELECTROLYTE COMPOSITION HAVING A REDUCED AIRBORNE EMISSION, METHOD AND USE OF THIS COMPOSITION

(71) Applicant: MacDermid Enthone Inc., Waterbury, CT (US)

(72) Inventor: Helmut Horsthemke, Solingen (DE)

(73) Assignee: MacDermid Enthone Inc., Waterbury, CT (US)

( * ) Notice: Subject to any disclaimer, the term of this patent is extended or adjusted under 35 U.S.C. 154(b) by 0 days.

(21) Appl. No.: 14/916,706

(22) PCT Filed: Sep. 5, 2014

(86) PCT No.: PCT/US2014/054368
§ 371 (c)(1),
(2) Date: Mar. 4, 2016

(87) PCT Pub. No.: WO2015/035219
PCT Pub. Date: Mar. 12, 2015

(65) Prior Publication Data
US 2016/0222534 A1 Aug. 4, 2016

(30) Foreign Application Priority Data
Sep. 5, 2013 (EP) .................... 13183142

(51) Int. Cl.
| C23C 18/16 | (2006.01) |
| C23C 18/31 | (2006.01) |
| C23C 18/34 | (2006.01) |
| C23C 18/36 | (2006.01) |
| C23C 18/40 | (2006.01) |
| C23C 18/44 | (2006.01) |
| C23C 18/52 | (2006.01) |
| C25D 3/02 | (2006.01) |
| C25D 3/10 | (2006.01) |
| C25D 3/12 | (2006.01) |
| C25D 3/20 | (2006.01) |
| C25D 3/22 | (2006.01) |
| C25D 3/26 | (2006.01) |
| C25D 3/32 | (2006.01) |
| C25D 3/38 | (2006.01) |
| C25D 3/46 | (2006.01) |
| C25D 3/48 | (2006.01) |
| C25D 3/52 | (2006.01) |
| C25D 3/54 | (2006.01) |
| C25D 21/12 | (2006.01) |
| C07C 317/04 | (2006.01) |

(52) U.S. Cl.
CPC .............. C25D 3/10 (2013.01); C07C 317/04 (2013.01); C23C 18/1675 (2013.01); C23C 18/31 (2013.01); C23C 18/36 (2013.01); C25D 3/02 (2013.01); C25D 21/12 (2013.01)

(58) Field of Classification Search
CPC ..... C23C 18/1675; C23C 18/31; C23C 18/34; C23C 18/36; C23C 18/40; C23C 18/44; C23C 18/52; C25D 3/02; C25D 3/10; C25D 3/12; C25D 3/20; C25D 3/22; C25D 3/26; C25D 3/32; C25D 3/38; C25D 3/46; C25D 3/48; C25D 3/52; C25D 3/54
USPC ......... 106/1.22, 1.23, 1.24, 1.25, 1.26, 1.27, 106/1.28, 1.29
See application file for complete search history.

(56) References Cited
U.S. PATENT DOCUMENTS

| 2,732,398 A * | 1/1956 | Brice et al. ............. B64C 11/42 205/430 |
| 2,750,334 A * | 6/1956 | Brown ..................... C25D 3/10 205/210 |
| 2,750,336 A * | 6/1956 | Brown ..................... C25D 3/10 205/290 |
| 2,750,337 A * | 6/1956 | Brown ..................... C25D 3/10 205/290 |
| 2,913,377 A * | 11/1959 | Brown ..................... C25C 1/00 205/331 |
| 4,484,990 A * | 11/1984 | Bultman ................... C25C 1/00 205/578 |
| 4,770,814 A * | 9/1988 | Rose .................... C10M 173/02 137/13 |

(Continued)

FOREIGN PATENT DOCUMENTS

| DE | 102007048142 | 4/2009 |
| FR | 2241542 | * 3/1975 |

(Continued)

OTHER PUBLICATIONS

Walters et al., "Uses of Perfluorinated Substances", Greenpeace Research Laboratories Jun. 2006; Sep. 2006; 20 pages.*
English translation of FR 2241542, Mar. 1975; 11 pages.*
English translation of JP 51/135836, Nov. 1976; 4 pages.*
English translation of JP 2008/266714, Nov. 2008; 13 pages.*
English translation of JP 2003/292989, Oct. 2003; 13 pages.*
English translation of JP 56/000504, Aug. 1981; 5 pages.*

(Continued)

Primary Examiner — Helene Klemanski
(74) Attorney, Agent, or Firm — Carmody Torrance Sandak & Hennessey LLP

(57) ABSTRACT

An aqueous electrolyte for the deposition of a metal layer on a substrate surface as well as a method for the deposition of a metal layer on a substrate surface by which electrolyte and in which method the formation of airborne emissions above the surface of the electrolyte in a plating tank is significantly reduced or more preferably omitted. The aqueous electrolyte composition according to the invention comprises at least one surfactant in a concentration affecting a dynamic surface tension of the composition of ≤35 mN/m.

25 Claims, 1 Drawing Sheet

(56) References Cited

U.S. PATENT DOCUMENTS

| | | | | |
|---|---|---|---|---|
| 4,849,059 A | * | 7/1989 | Deresh | C25D 3/32 205/254 |
| 5,468,353 A | | 11/1995 | Anich et al. | |
| 5,624,541 A | * | 4/1997 | Pohmer | C25D 3/10 205/52 |
| 6,833,479 B2 | * | 12/2004 | Witschger | C07C 217/28 205/585 |
| 6,837,981 B2 | * | 1/2005 | Horsthemke | C25D 3/10 205/243 |
| 7,846,503 B2 | * | 12/2010 | Stark | C23C 18/36 427/345 |
| 2003/0070934 A1 | | 4/2003 | Cobley et al. | |
| 2003/0111349 A1 | * | 6/2003 | Sierakowski | C25C 1/00 205/67 |
| 2007/0131558 A1 | * | 6/2007 | Horsthemke | C25D 3/10 205/283 |
| 2011/0198226 A1 | * | 8/2011 | Horsthemke | C25D 5/04 205/50 |
| 2011/0290656 A1 | | 12/2011 | Laser et al. | |
| 2013/0056357 A1 | * | 3/2013 | Virnig | C25D 3/38 205/67 |

FOREIGN PATENT DOCUMENTS

| | | | |
|---|---|---|---|
| FR | 2241542 A1 | | 3/1975 |
| FR | 2 241 542 | * | 4/1975 |
| GB | 1529104 | | 10/1978 |
| GB | 2105370 A | * | 3/1983 |
| JP | 42-018204 | | 9/1942 |
| JP | 51-135836 | | 11/1976 |
| JP | 54076443 | | 6/1979 |
| JP | 58-042786 | | 3/1983 |
| JP | 02-107793 | | 4/1990 |
| JP | 2003-292989 | | 10/2003 |
| JP | 2008-266714 | | 11/2008 |
| WO | 2009046427 | | 4/2009 |

OTHER PUBLICATIONS

Author: Du Pont de Nemours (Nederland) B.V. Title: Capstone FS-10 Fluorosurfactant SDS. pp. 1-12. Publication Date: Dec. 20, 2012. Publisher: Du Pont De Nemours (Nederland) B.V., Baanhoekweg 22, NL-3313 LA Dordrecht, Netherlands. Place of Publication: Publically available via the internet as of Dec. 20, 2012.

Technical Data Sheet, Ankor® 1127, Hard Chrome Plating Process, MacDermid Enthone Industrial Solutions, Jun. 3, 2016, Version 2.1.

Federal Register, vol. 77, No. 182, Sep. 19, 2012, Part II, Environmental Protection Agency, National Emission Standards for Hazardous Air Pollutant Emissions: Hard and Decorative Chromium Electroplating and Chromium Anodizing Tanks; and Steel Pickling-HCl Process Facilities and Hydrochloric Acid Regeneration Plants; Final Rules.

Safety Data Sheet, Capstone® FS-10 Fluorosurfactant, DuPont de Nemours (Nederland) B.V., Apr. 8, 2011, Version 3.0.

Technical Information, Dupont Capstone® FS-10, Fluorinated Surfactant, Dupont Chemical Solutions Enterprise, Jul. 2008.

Encyclopedic Dictionary of Chemistry 9, p. 78, Feb. 15, 1987, the 30th print.

* cited by examiner

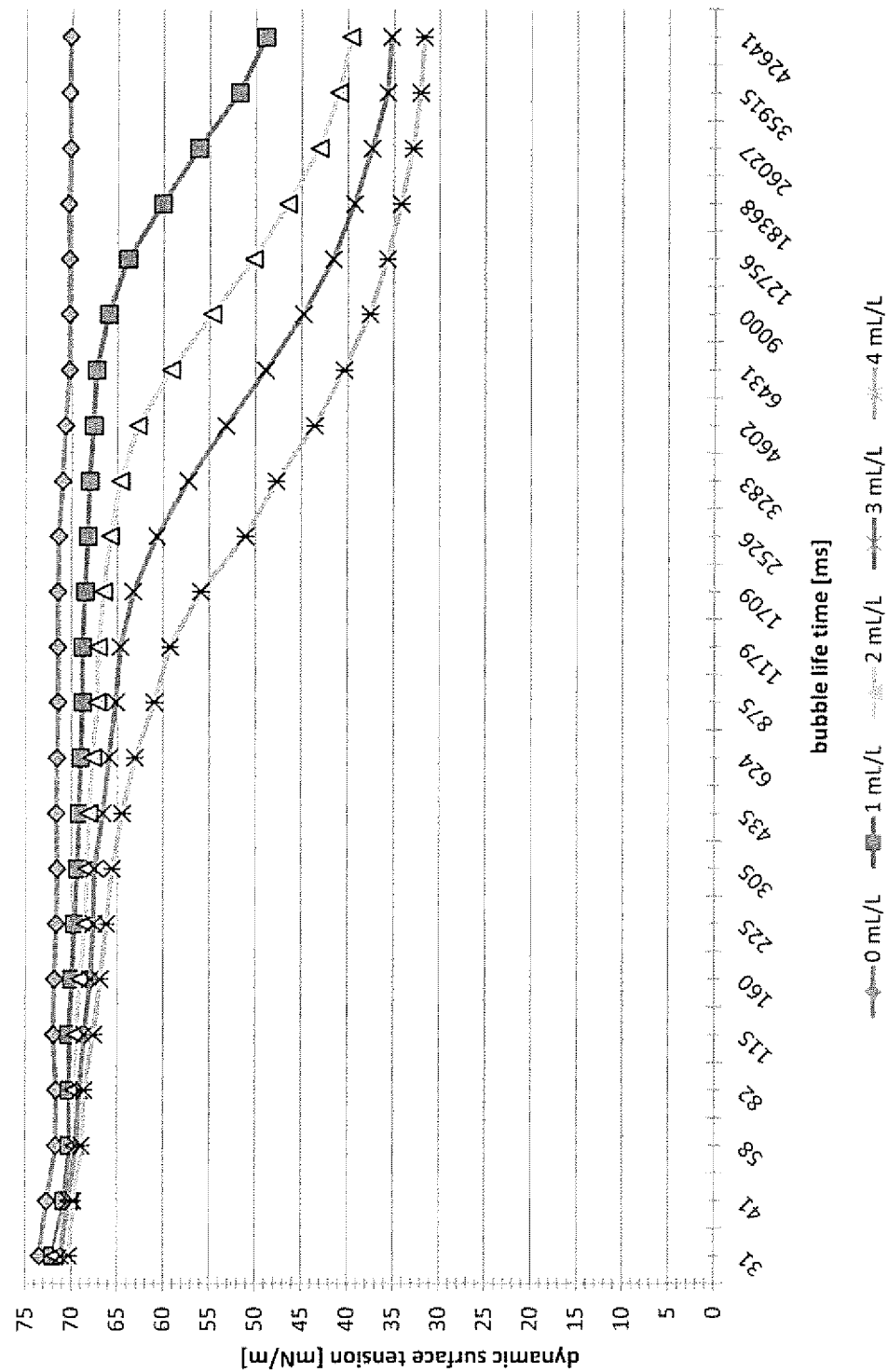

AQUEOUS ELECTROLYTE COMPOSITION HAVING A REDUCED AIRBORNE EMISSION, METHOD AND USE OF THIS COMPOSITION

FIELD OF THE INVENTION

The present invention relates to an aqueous electrolyte composition for the deposition of a metal layer on a substrate surface, said aqueous electrolyte composition having a reduced airborne emission. Furthermore, the invention relates to a method for the deposition of a metal layer on a substrate surface in which method the formation of airborne emission is reduced.

BACKGROUND OF THE INVENTION

The deposition of metal layers on substrate surfaces is a well-known technique in the art to modify features of surfaces, like e.g. the optical appearance of the surface, the wear resistance, or the corrosion resistance of the surface. For the deposition of a metal layer on the substrate surface the surface is brought into contact with an adequate plating solution. In general, such plating solutions are aqueous electrolyte compositions comprising ions of the metal to be deposited as well as additional additives for the optimization of the plating reaction or the features of the metal layer deposited.

For the deposition of a metal layer on a substrate surface from an electrolyte comprising the metal to be deposited as an ion, a source of electrons is needed to induce the electrochemical reaction resulting in the metal deposition. Such source for electrons may be a reduction agent or an external current supplied to the substrate and a counter electrode. The deposition under utilization of a reduction agent is known as autocatalytic process or electroless plating. While electroless plating is used in various applications, especially for decorative issues, the metal deposition under use of an external current is often used for the deposition of metal layers having increased wear resistance or corrosion resistance of the surface.

In general, when it comes to the deposition of metal layers under use of an external electric current—in the following also referred to as electrolytic deposition—highly acidic or highly alkaline electrolyte compositions are used.

A principal problem associated with such electrolytic deposition is the occurrence of acidic or alkaline mist which is caused by the generation of gases, like e.g. hydrogen or oxygen, during the electrolytic deposition process. This mist is a healthy hazard and various ways of suppressing it have been attempted, incorporating mechanical and chemical approaches.

One chemical approach is to create a foam layer on the surface of the electrolyte used. This foam layer acts like a blanket to reduce airborne emissions of hazardous mist. However, a drawback of such foam layers is the accumulation of highly flammable gases, like e.g. hydrogen or oxygen, within the foam. To avoid explosions of the foam the equipment used for the plating process must comprise an explosion prove electrically installation. Furthermore, any kind of electrostatic charge which may cause some electrical sparks must be avoided. Both, the explosion proved electrically installation as well as the additional facilities to avoid electrostatic charge cause additional costs when setting up the plating system.

As a mechanical alternative to such foam layers, or in addition, exhaustions are used for the plating facilities. However, such exhaustion must be explosion proved, too.

UK Patent Application GB 2 250 515 A discloses a method for the electrolytic recovery of metal which comprises electrolyzing an acidic solution of the metal, the solution containing dissolved therein an ionic or cationic polyelectrolyte which is ionized under the electrolytic conditions employed and which possesses a hydrophobic moiety in the molecule such that the surface tension of the surface of the bath is reduced sufficiently to produce a foam.

US 2003/0111349 A1 discloses electrolytic solutions containing organic additives selected from a described class of additives (like e.g. 4,6-dihydroxypyrimidine) to reduce gas formation at the anodes of an electrolytic deposition process.

U.S. Pat. No. 5,468,353 discloses that the formation of acid mist or spray over metal electrowinning tanks, such as in the electrowinning of copper obtained by solvent extraction, is substantially inhibited or eliminated by electrowinning the metal from electrolytes containing certain fluoroaliphatic non-foam forming surfactants.

U.S. Pat. No. 4,484,990 discloses that the formation of acid mist or spray over metal electrowinning tanks, such as in the electrowinning of copper obtained by solvent extraction, is substantially inhibited or eliminated by electrowinning the metal from electrolytes containing certain cationic and/or amphoteric fluoroaliphatic surfactants.

US 2013/0056357 A1 discloses acid mist mitigation agents for electrolyte solutions. Sulfonates-, sulfate-, or carboxylate-caped, alcoxylated anti-misting agents are disclosed for use in a method of suppressing mist from electrolyte solutions.

SUMMARY OF THE INVENTION

However, all of the attempts taken in the state of the art show various drawbacks, like e.g. environmental shortcomings of the surfactants used. It is therefore an object of the invention to provide an improved aqueous electrolyte composition for the deposition of a metal layer on a substrate surface reducing airborne emission.

Another object of the invention is to provide the method for the deposition of a metal layer on a substrate surface in which a method the formation of airborne emission is significantly reduced or eliminated.

With respect to the aqueous electrolyte composition the object of the invention is solved by a composition according to the present invention.

BRIEF DESCRIPTION OF THE FIGURES

The FIGURE depicts the result of a measurement made of a bubble pressure tensiometer at 20° C.

DETAILED DESCRIPTION OF PREFERRED EMBODIMENTS

Hence, an aqueous electrolyte composition for the deposition of a metal layer on a substrate surface is provided, said composition comprising at least ions of the metal to be deposited and at least one surfactant, wherein the surfactant is comprised in a concentration effecting a dynamic surface tension of the composition of ≤35 mN/m, preferably of <33 mN/m, most preferred of ≤30 mN/m.

Surprisingly, it was found that the dynamic surface tension of a composition influences the formation of airborne emissions. If was found that setting the dynamic surface tension of the composition to a value ≤35 mN/m significantly reduces the formation of airborne emission so that hazardous mists can be reduced or even avoided. The airborne emission is caused by gas bubbles created at the electrodes which arise to the surface of the electrolyte. At the surface, these bubbles expand above the liquid and break, thereby releasing entrapped gas into the atmosphere. The liquid in the gas bubble wall just before it breaks is made-up of the electrolyte solution. As the liquid wall ruptures, it disintegrates into extremely small droplets that readily become airborne. The macroscopic effect of this procedure is to create an aggressive mist above the plating tank. Such mist readily can migrate throughout the workplace.

By reducing the dynamic surface tension of the electrolyte composition to a value below 35 mN/m the gas bubbles produced at the electrodes became very small. Due to the reduction of the size of the gas bubbles the liquid wall of the bubbles became much thinner which in turn leads to reduced forces when the bubbles disintegrate on the surface of the electrolyte composition. While not being bound to this theory the applicant believes that this reduced force at the time of disintegration on one hand together with a reduced amount of liquid in the liquid wall of the bubbles on the other hand causes the beneficial effect of reduction or avoidance of airborne emission.

The dynamic surface tension relevant for the aqueous electrolyte composition may be measured by a method known as bubble pressure tensiometry making use of a bubble pressure tensiometer. In a bubble pressure tensiometer gas bubbles are produced at a defined bubble formation rate in the solution to be analyzed. The gas bubbles are introduced into the solution by a capillar having a known radius. The pressure within the capillar is measured. During the process the pressure will pass a maximum which will be recognized by the system. This detection method is highly comparable to the effects of gas formation during an electrolytic plating process and therefore most relevant to the question of avoidance of airborne emission.

According to a preferred embodiment of the invention the surfactant used in the inventive aqueous electrolyte composition is at least one surface of the general formula $C_NF_MH_ZSO_2X$, wherein N is an integer between ≥6 and ≤22, preferably between ≥7 and ≤20, M is ≤2N, Z=2N+1−M, and X is one of F, Cl, or Br. Surprisingly it was found that such non-perfluorinated but partially fluorinated surfactants are capable to provide a dynamic surface tension within the claimed range while at same time being environmentally harmless. An example for a surfactant according to the above-mentioned general formula is 3,3,4,4,5,5,6,6,7,7,8,8,8-tridecafluoroctansulphonyl chloride. This is available, for example, from E.I. du Pont de Nemours under the tradename DuPont Capstone Fluorosurfactant FS-10. In preferred embodiments, the electrolyte composition comprises the partially fluorinated surfactant which is also polyfluorinated, and the electrolyte composition is free of any perfluorinated compounds.

According to another embodiment of the invention the partially fluorinated surfactant is comprised in the electrolyte composition in a concentration range between ≥0.0000001% by weight and ≤0.000002% by weight, preferably between ≥0.0000004% by weight and ≤0.0000015% by weight.

In a preferred embodiment of the invention the dynamic surface tension of the composition is measured at standard temperature, i.e. 20° C.

According to another preferred embodiment of the invention the electrolyte composition comprises an anti-foaming agent. In an even more preferred embodiment of the invention the anti-foaming agent is a water-based composition comprising at least one acid selected from the group consisting of hydrochloride acid, sulfuric acid, alkanesulfonic acid, phosphoric acid, phosphonic acid, malonic acid, malic acid, and lactic acid, and at least one ester of a halogenated alcohol according to the general formula CNXMHzOH, wherein N is an integer between >6 and ≤22, preferably >6 and ≤18, X is F, Cl, or Br, N≤2N, and Z=2N+1−M.

The addition of an anti-foaming agent avoids the formation of a foam layer on the surface of the electrolyte composition, in which foam layer otherwise explosive gases, like e.g. hydrogen or oxygen, may accumulate.

Preferably, the anti-foaming agent can be comprised in the electrolyte composition in a concentration range of between >0.0001% by weight and ≤0.0005% by weight, preferably between >0.0002% by weight and ≤0.002% by weight, more preferably between >0.0002% by weight and ≤0.001% by weight, and most preferably between ≥0.0001% by weight and ≤0.005% by weight.

According to another preferred embodiment of the invention the composition comprises a sulfonic acid according to the general formula $C_NF_NH_ZSO_2OH$, wherein N is an integer between ≥6 and ≤22, preferably between ≥7 and ≤20, M≤2N, and Z=2N+1−M.

Preferably, the sulfonic acid can be comprised in the electrolyte composition in a concentration range of between >0.0008% by weight and ≤0.0005% by weight, preferably between >0.0001% by weight and ≤0.0025 by weight, more preferably between >0.0012% by weight and ≤0.002% by weight, more preferably between ≥0.001% by weight and ≤0.0025% by weight or more preferably between ≥0.0008% by weight and ≤0.005% by weight.

While the electrolyte composition according to the invention may be applicable for any kind of metal to be deposited on a substrate surface in a preferred embodiment of the invention the metal to be deposited and of which ions are comprised in the electrolyte composition is at least one metal selected from the group consisting of copper (Cu), Nickel (Ni), chrome (Cr), silver (Ag), gold (Au), platinum (Pt), zinc (Zn), iron (Fe), Indium (In), Gallium (Ga), Tungsten (W), Selenium (Se), Tellurium (Te), Manganese (Mn), Bismuth (Bi), Cobalt (Co), Tin (Sn), and Cadmium (Cd).

In another aspect the invention is directed to a method. Hence, a method for the deposition of a metal layer on a substrate surface is provided, said method comprising the steps of:

- providing a substrate on which a metal layer should be deposited;
- providing an aqueous electrolyte composition according to the invention as described above;
- bringing into contact the aqueous electrolyte composition with a surface of a substrate on which the metal layer should be deposited;
- wherein the step of providing the aqueous electrolyte composition comprises the steps of:
- providing an aqueous base electrolyte, said base electrolyte comprising at least ions of the metal to be deposited in a concentration sufficient to enable a metal layer deposition; and
- adding to said base electrolyte an aqueous surfactant composition, wherein said surfactant composition comprises at least one surfactant of the general formula $C_NF_NH_ZSO_2X$, wherein N is an integer between ≥6 and ≤22, preferably between ≥7 and ≤20, M≤2N, Z=2N+1−M, and X is one of F, Cl, or Br, and at least one anti-foaming agent being a water-based composition comprising at least one acid selected from the group consisting of hydrochloric acid, sulfuric acid, phosphoric acid, phosphonic acid, malonic acid, malic acid, and lactic acid, and at least one ester of a halogenated alcohol according to the general formula $C_NX_MH_ZOH$, wherein N is an integer between ≥6 and ≤22, preferably between ≥6 and ≤18, X is F, Cl, or Br, M≤2N, and Z=2N+1−M, and at least one sulfonic acid according to the general formula $C_NF_MH_ZSO_2OH$, wherein N is an integer between ≥6 and ≤22, preferably between ≥7 and ≤20, M≤2N, and Z=2N+1−M, wherein the aqueous surfactant composition is added to the base electrolyte to provide a dynamic surface attention of ≤35 mN/m.

According to a preferred embodiment of the invention, the method comprises the step of maintaining the dynamic surface tension of the aqueous electrolyte composition at a level of ≤35 mN/m by continuous or occasional addition of the aqueous surfactant composition as described above.

According to another preferred embodiment of the invention, the metal to be deposited is at least one metal selected from the group consisting of Cu, Ni, Cr, Ag, Au, Pt, Zn, Fe, In, Ga, W, Se, Te, Mn, Bi, Co, Sn, and Cd.

According to another embodiment of the invention, the deposition of the metal layer on the substrate surface is performed autocatalytically by addition of at least one reduction agent to the base electrolyte prior to contacting the substrate surface with the electrolyte composition. Alternatively, the deposition is performed galvanically by applying a current between the substrate and an anode.

According to another aspect of the invention the use of a surfactant composition in an electrolyte for the deposition of at least one metal selected from the group consisting of Cu, Ni, Cr, Ag, Au, Pt, Zn, Fe, In, Ga, W, Se, Te, Mn, Bi, Co, Sn, and Cd, is disclosed, wherein said surfactant composition comprises at least one surfactant of the general formula $C_NF_MH_ZFO_2X$, wherein N is an integer between ≥6 and ≤22, preferably between ≥7 and ≤20, M≤2 N, Z=2N+1−M, and X is one of F, Cl, or Br, at least one anti-foaming agent being a water-based composition comprising at least one acid selected from the group consisting of hydrochloric acid, sulfuric acid, alkane sulfuric acid, phosphoric acid, phosphonic acid, malonic acid, malic acid, and lactic acid, and at least one ester of a halogenated alcohol according to the general formula $C_NX_MH_ZOH$, wherein N is an integer between ≥6 and ≤22, preferably between ≥6 and ≤18, X is F, Cl, or Br, M2N, and Z=2N+1−M, and at least one sulfonic acid according to the general formula $C_NF_NH_ZSO_2OH$, wherein N is an integer between ≥6 and ≤22, preferably between ≥7 and ≤20, M≤2N, and Z=2N+1−M.

According to another aspect of the invention, the aqueous electrolyte composition for the deposition of a metal layer on a substrate surface in an alkaline zinc plating process, wherein the solution prepared in a dissolving compartment separate from a plating tank in which dissolving compartment zinc sheets or rods are dissolved in a high alkaline solution. Generally, during such dissolving a high gassing occurs which causes airborne emissions. By providing at least one surfactant in a concentration effecting a dynamic surface tension of the composition of ≤35 mN/m, preferably of ≤33 mN/m, most preferred of ≤30 mN/m the formation of airborne emission can significantly be reduced, so that coverage of the dissolving compartment can be avoided.

The invention is further described by embodiments and FIGURES, while neither the embodiments nor the FIGURES have any limiting character to the scope of the invention.

Example 1

To a base electrolyte consisting of 300 g/l chromic acid, 3.75 g/l sulfate (added as sulfuric acid), and 50 mill of a catalyst (ANKOR 1127 make up solution, available from Enthone Inc.), methane disulfonic acid was added in various concentrations, i.e. 0 ml/l, 1 ml/l, 2 ml/l, 3 ml/l, and 4 ml/l. The dynamic surface tension of the resulting mixture was measured by a bubble pressure tensiometer at 20° C. The results are shown in the FIGURE.

The FIGURE shows the result of a measurement made under us of a bubble pressure tensiometer (SITA science line t60) at 20° C. The bubble lifetime is measured. That allows calculating the dynamic surface tension. Surface tension is created through the attraction of the molecules in liquids to each other. If one views a molecule at the interior of a medium, it would be equally attracted by all neighboring molecules. The effect is that it is attracted to all sides with the same force, so that the resulting force is zero. On the other hand, if a molecule is located at the surface of a liquid, the attraction from the interior of the medium works further on the one side, whereas there are no more molecules from the other side. Hence the resulting force is directed towards the interior of the liquid. On the microscopic scale this causes drops of liquid to be round since the surface of the liquid is being minimized that way. Therefore, surface tension is defined as the energy needed to increase the surface by a defined value, whereby the minimum surface corresponds to the minimum energy. Through the attraction between the molecules of the testing liquid, air bubbles within the liquid are also subject to these forces i.e. a bubble formed within a liquid is being compressed by the surface tension. The resulting pressure rises with the decreasing bubble radius. This increased pressure, in comparison to the outside of the bubble, is used to measure surface tension. Air is pumped through a capillary into a liquid. The surface of the bubble so created bulges and the bubble radius continuously decreases. During this process the pressure rises to a maximum at which the bubble has its smallest radius. This radius equals the radius of the capillary and forms a half sphere. After passing this point the bubble bursts and breaks away from the capillary. Now, a new bubble can form at the tip of the capillary. During this process the characteristic course of pressure in the bubble can be measured. From this characteristic course of pressure the surface tension can be calculated.

Example 2

An electroless nickel bath with 15 g/l nickel, 40 g/l sodium hypophosphite, 35 g/l hydroxy carboxylic acid (e.g. lactic acid), 2.5 g/l hydroxy polycarboxylic acid (e.g. malonic acid), 1 g/l potassium iodide and 0.5 mg/l stabilizer (antimony, added as antimony chloride) was used and 0.0008% by weight anti-foaming agent was added. There was not observed any airborne emission by the evolved hydrogen.

Example 3

To a base electrolyte consisting of 300 g/l chromic acid, 3.75 g/l sulfate (added as sulfuric acid), and 50 ml/l of a catalyst (ANKOR 1127 make up solution, available from Enthone Inc.), 3,3,4,4,5,5,6,6,7,7,8,8,8-tridecafluoroctan-sulphonyl chloride is added in various concentrations up to about 4 ml/l, such as between 1 ml/L and 4 ml/L, e.g., 0 ml/L, 1 ml/L, 2 ml/L, 3 ml/L, and 4 ml/L. There is not observed any airborne emission by the evolved hydrogen when using the electrolyte in a chromium plating process.

Example 4 (Comparison)

To a base electrolyte consisting of 300 g/l chromic acid, 3.75 g/l sulfate (added as sulfuric acid), and 50 ml/l of a catalyst (ANKOR 1127 make up solution, available from Enthone Inc.), 3,3,4,4,5,5,6,6,7,7,8,8,8-tridecafluoroctansulphonyl chloride is added in various concentrations up to about 4 ml/l. Additionally, a further surfactant is added, e.g. a perfluorinated phosphonic acid ester in a concentration of 8 ml/l. The dynamic surface tension of the resulting mixture is measured by a bubble pressure tensiometer at 20° C. There is significant airborne emission observed by the evolved hydrogen when using the electrolyte in a chromium plating process.

When introducing elements of the present invention or the preferred embodiment(s) thereof, the articles "are", "an", "the" and "said" are intended to mean that there are one or more of the elements. The terms "comprising", "including" and "having" are intended to be inclusive and mean that there may be additional elements or other than the listed elements.

As various changes could be made in the above without departing from the scope of the invention, it is intended that all matter contained in the above description and shown in the accompanying FIGURES shall be interpreted as illustrative and not in a limiting sense. The scope of the invention is defined by the appendant claims and modification to the embodiments above may be made that do not depart from the scope of the invention.

The invention claimed is:

1. An aqueous electrolyte composition for the deposition of a metal layer on a substrate surface, wherein the composition comprises at least ions of the metal to be deposited and at least one surfactant which is partially fluorinated and is not perfluorinated, wherein the surfactant is comprised in a concentration effecting a dynamic surface tension of the composition of ≤35 mN/m at 20° C.,
wherein the surfactant is at least one surfactant of the general formula $C_NF_MH_ZSO_2X$, wherein N is an integer between ≥6 and ≤22, M≤2N, Z=2N+1−M, and X is one of F, Cl, or Br; and
wherein the surfactant is comprised in a concentration range between ≥0.0000001% by weight and ≤0.000002% by weight.

2. The electrolyte composition according to claim 1, wherein the composition comprises an anti-foaming agent.

3. The electrolyte composition according to claim 2, wherein the anti-foaming agent is a water based composition comprising at least one acid selected from the group consisting of hydrochloric acid, sulfuric acid, alkanesulfonic acid, phosphoric acid, phosphonic acid, malonic acid, malic acid, and lactic acid, and at least one ester of a halogenated alcohol according to the general formula $C_NX_MH_ZOH$, wherein N is an integer between ≥6 and ≤22, X is F, Cl, or Br, M≤2N, and Z=2N+1−M.

4. The electrolyte composition according to claim 3, wherein the anti-foaming agent is comprised in a concentration range of between ≥0.0001% by weight and 0.005% by weight.

5. The electrolyte according to claim 1, wherein the composition comprises a sulfonic acid according to the general formula $C_NF_MH_ZSO_2OH$, wherein N is an integer between ≥6 and ≤22, M≤2N, and Z=2N+1−M.

6. The electrolyte composition according to claim 5, wherein the sulfonic acid is comprised in a concentration range of between ≥0.0008% by weight and ≤0.005% by weight.

7. The electrolyte composition according to claim 1, wherein the metal to be deposited and of which ions are comprised in the electrolyte composition is at least one metal selected from the group consisting of Cu, Ni, Cr, Ag, Au, Pt, Zn, Fe, In, Ga, W, Se, Te, Mn, Bi, Co, Sn, and Cd.

8. The electrolyte composition according to claim 7, wherein the metal ions are Cr ions.

9. The electrolyte composition according to claim 1, wherein the composition is free of perfluorinated compounds.

10. The electrolyte composition of claim 1, comprising the following:
a compound of the general formula $C_NF_MH_ZSO_2X$ as the partially fluorinated surfactant,
wherein N is an integer between ≥6 and ≤22, M≤2N, Z=2N+1−M, and X is one of F, Cl, or Br,
wherein the compound is present in a concentration between ≥0.0000004% by weight and ≤0.0000015% by weight;
Zn ions or Cr ions as the metal ions;
wherein the electrolyte composition is free of perfluorinated compounds.

11. The electrolyte composition according to claim 10, wherein the partially fluorinated surfactant is 3,3,4,4,5,5,6,6,7,7,8,8,8-tridecafluoroctansulphonyl chloride.

12. The electrolyte composition according to claim 1, wherein the surfactant is comprised in a concentration effecting a dynamic surface tension of the composition of ≤33 mN/m at 20° C.

13. The electrolyte composition according to claim 12, wherein the surfactant is comprised in a concentration effecting a dynamic surface tension of the composition of ≤30 mN/m at 20° C.

14. The electrolyte composition according to claim 2, wherein N is an integer between ≥7 and ≤20.

15. The electrolyte composition according to claim 3, wherein the surfactant is comprised in a concentration range between ≥0.0000004% by weight and ≤0.0000015% by weight.

16. The electrolyte composition according to claim 3, wherein N is an integer between ≥6 and ≤18.

17. The electrolyte composition according to claim 4, wherein the anti-foaming agent is comprised in a concentration range of between ≥0.0002% by weight and ≤0.002% by weight.

18. The electrolyte composition according to claim 17, wherein the anti-foaming agent is comprised in a concentration range of between ≥0.0002% by weight and ≤0.001% by weight.

19. The electrolyte composition according to claim 5, wherein N is an integer between ≥7 and ≤20.

20. The electrolyte composition according to claim 6, wherein the sulfonic acid is comprised in a concentration range of between ≥0.001% by weight and ≤0.0025% by weight.

21. A method for the deposition of a metal layer on a substrate surface, said method comprising the steps of:
a) providing a substrate on which the metal layer should be deposited;

b) providing an aqueous electrolyte composition for the deposition of the metal layer on the substrate surface, wherein the composition comprises
  i) at least ions of the metal to be deposited, and
  ii) an aqueous surfactant composition, wherein the aqueous surfactant composition comprises:
   (a) at least one surfactant of the general formula $C_NF_MH_ZSO_2X$, wherein N is an integer between ≥6 and ≤22, M≤2N, Z=2N+1−M, and X is one of F, Cl, or Br, wherein the at least one surfactant is partially fluorinated and is not perfluorinated;
   (b) at least one anti-foaming agent being a water based composition comprising at least one acid selected from the group consisting of hydrochloric acid, sulfuric acid, alkanesulfonic acid, phosphoric acid, phosphonic acid, malonic acid, malic acid, and lactic acid; and
   (c) at least one ester of a halogenated alcohol according to the general formula $C_NX_MH_ZOH$, wherein N is an integer between ≥6 and ≤22, X is F, Cl, or Br, M≤2N, and Z=2N+1−M; and
   (d) at least one sulfonic acid according to the general formula $C_NF_MH_ZSO_2OH$, wherein N is an integer between ≥6 and ≤22, M≤2N, and Z=2N+1−M,
  wherein the aqueous surfactant composition is added to the aqueous electrolyte composition to provide a dynamic surface tension of ≤35 mN/m at 20° C.; and
c) bringing into contact the aqueous electrolyte composition with the surface of the substrate on which the metal layer should be deposited.

22. The method according to claim 21, wherein said method comprises the step of maintaining the dynamic surface tension of the aqueous electrolyte composition at ≤35 mN/m at 20° C. by addition of the aqueous surfactant composition.

23. The method according to claim 21, wherein the metal to be deposited is at least one metal selected from the group consisting of Cu, Ni, Cr, Ag, Au, Pt, Zn, Fe, In, Ga, W, Se, Te, Mn, Bi, Co, Sn, and Cd.

24. The method according to claim 21, wherein the deposition is performed autocatalytically by addition of at least one reduction agent to the aqueous electrolyte composition.

25. The method according to claim 21, wherein the deposition is performed galvanically by applying a current between the substrate and an anode.

* * * * *